United States Patent [19]

Schehlmann et al.

[11] Patent Number: 5,897,870
[45] Date of Patent: Apr. 27, 1999

[54] AQEOUS OR AQUEOUS-ALCOHOLIC HAIR-COSMETIC FORMULATION

[75] Inventors: Volker Schehlmann, Römerberg; Peter Hössel, Schifferstadt, both of Germany

[73] Assignee: BASF Aktiengesellschaft, Ludwigshafen, Germany

[21] Appl. No.: 08/931,182

[22] Filed: Sep. 16, 1997

[30] Foreign Application Priority Data

Sep. 20, 1996 [DE] Germany .................. 196 38 795

[51] Int. Cl.⁶ .................................................. A61K 7/11
[52] U.S. Cl. .................... 424/70.122; 424/70.11; 424/70.21; 424/70.22; 424/70.27
[58] Field of Search ........................ 424/78.02, 401, 424/45, 47, 70.11, 70.122, 70.22, 70.21, 70.27

[56] References Cited

U.S. PATENT DOCUMENTS 3,577,517  5/1971  Ikuo et al. ........................... 424/47
4,192,861  3/1980  Micchelli et al. .................... 424/47
4,842,852  6/1989  Nowak et al. ...................... 526/307.6

FOREIGN PATENT DOCUMENTS 590 604    4/1994   European Pat. Off. .
28 16 504  11/1979  Germany .
43 14 305  11/1994  Germany .

Primary Examiner—Thurman K. Page
Assistant Examiner—N. Levy
Attorney, Agent, or Firm—Keil & Weinkauf

[57] ABSTRACT

An aqueous or aqueous-alcoholic hair-cosmetic formulation comprising as film former copolymers based on (meth)acrylate which have a K value of 20–150 are obtainable by free-radical polymerization of (a) 40–65% by weight of acrylic acid and/or methacrylic acid,
(b) 14–60% by weight of alkyl (meth)acrylate, and
(c) 0–50% by weight of a further free-radically polymerizable monomer or a mixture thereof;

20–100% of the carboxyl groups of the copolymer being neutralized.

6 Claims, No Drawings

AQEOUS OR AQUEOUS-ALCOHOLIC HAIR-COSMETIC FORMULATION

The present invention relates to aqueous or aqueous-alcoholic hair-cosmetic formulations which comprise (meth) acrylate-based copolymers as film former.

DE 29 17 504 describes aerosol hairsprays based on a resin whose monomer content includes 5–55 mol % of carboxyl-containing monomers. The carboxylate groups are neutralized with long-chain amines to improve the solubility of the resin in alcohol/hydrocarbon propellants. It is precisely in the environmentally more favorable water-based formulations, however, that long-chain amines are unsuitable for neutralization, since they diminish water-solubility and washout.

DE 43 14 305 describes hairsetting compositions that are based on polymers and include, in addition to tert-butyl (meth)acrylate, also 10–28% by weight of acrylic or methacrylic acid.

U.S. Pat. No. 4,196,190 describes hairsetting resins which in addition to three other monomers comprise 12–30% by weight of methacrylic acid.

EP 590 604 describes an acrylate dispersion for use in hair-sprays, where the copolymer contains at least 60% by weight of (meth)acrylic ester and 1–15% by weight of acrylic acids.

U.S. Pat. No. 3,577,517 describes polymers for hair lacquers which include from 6 to 37% by weight of acrylic or methacrylic acid.

A disadvantage of the copolymers described above is, however, that to be washed out of the hair with sufficient ease it is necesssary to neutralize more than 90% of the acid groups. A consequence of this high degree of neutralization, however, is that the pH of the formulation becomes greater than 8, which in the case in particular of hair mousses, hair gels, hair lotions or hairsetting solutions—ie. formulations which come into contact, sometimes intensely, with the skin—there may be instances of slight skin irritation in sensitive people.

A further disadvantage of the known copolymers containing acrylic and/or methacrylic acid is the comparatively poor dry combability of the treated hair. To improve the dry combability use has been made to date of additional appropriate formulation ingredients, for example polysiloxanes, which nevertheless increase the costs of the formulation.

It is an object of the present invention, therefore, to provide polymers based on (meth)acrylic acid that can be used in ecologically enhanced, water-containing formulations with a pH of less than 8 and yet are easy to wash out from the hair and also possess such good dry combability that it is unnecessary to use additional substances for assistance.

We have found that this object is achieved by aqueous or aqueous-alcoholic hair-cosmetic formulations comprising as film former copolymers based on (meth)acrylate which have a K value of 20–150 and are obtainable by free-radical polymerization of (a) 40–65% by weight of acrylic acid and/or methacrylic acid,
(b) 14–60% by weight of one or more alkyl (meth) acrylates, and
(c) 0–50% by weight of one or more free-radically polymerizable monomers, 20–100% of the carboxyl groups of the copolymer being neutralized.

Particularly preferred hair-cosmetic formulations are those in which the copolymer comprises (a) 45–60% by weight of acrylic acid and/or methacrylic acid and where 20–80%, especially 20–60%, of the carboxyl groups of the copolymer are neutralized.

Suitable alkyl (meth)acrylates (b) are:

esters of (meth)acrylic acid with $C_1$–$C_{30}$-alkyl alcohols, for example methyl methacrylate, ethyl acrylate, ethyl methacrylate, n-propyl acrylate, n-propyl methacrylate, isopropyl acrylate, isopropyl methacrylate, n-butyl acrylate, n-butyl methacrylat, isobutyl acrylate, isobutyl methacrylate, t-butyl acrylate, t-butyl methacrylate, pentyl acrylate, pentyl methacrylate, n-hexyl acrylate, n-hexyl methacrylate, n-heptyl acrylate, n-heptyl methacrylate, n-octyl acrylate, n-octyl methacrylate, 2-ethylhexyl acrylate, 2-ethylhexyl methacrylate, decyl acrylate, decyl methacrylate, lauryl acrylate, lauryl methacrylate, palmityl acrylate, palmityl methacrylate, stearyl acrylate, stearyl methacrylate, hydrenol (meth) acrylate, behenyl (meth)acrylate, polyisobutene (meth) acrylate, phenoxyethyl acrylate or phenoxyethyl methacrylate, or $C_5$–$C_6$-cycloalkyl (meth)acrylates, in which the cycloalkyl can be substituted by 1, 2 or 3 $C_1$–$C_4$-alkyls, examples being cyclohexyl acrylate, cyclohexyl methacrylate, 4-methylcyclohexyl acrylate and 4-methylcyclohexyl methacrylate.

Preference is given to C1–C4-alkyl (meth)acrylates.

The esters (b) are employed in the copolymers in an amount of 14–60% by weight, preferably 20–55% by weight, based on the overall weight of all monomers.

Both individual compounds and mixtures of individual compounds can be employed as monomers (b).

Suitable free-radically polymerizable monomers (c) are, preferably, unsubstituted or N-C1–C18-alkyl- or -hydroxyalkyl-substituted (meth)acrylamides, such as acrylamide, methacrylamide, N-methylacrylamide, N-methylmethacrylamide, N-ethylacrylamide, N-ethylmethacrylamide, N-propylacrylamide, N-propylmethacrylamide, N-isopropylacrylamide, N-isopropylmethacrylamide, N-n-butylacrylamide, N-n-butylmethacrylamide, N-isobutylacrylamide, N-isobutylmethacrylamide, N-t-butylacrylamide, N-t-butylmethacrylamide, N-pentylmethacrylamide, N-hexylacrylamide, N-hexylmethacrylamide, N-heptylacrylamide, N-heptylmethacrylamide, N-octylacrylamide, N-octylmethacrylamide, N-2-ethylhexylacrylamide, N-2-ethylhexylmethacrylamide, N-nonylacrylamide, N-nonylmethacrylamide, N-decylacrylamide, N-decylmethacrylamide, N-laurylacrylamide, N-laurylmethacrylamide, N-palmitylacrylamide, N-palmitylmethacrylamide, stearylacrylamide, N-stearylmethacrylamide, N-hydroxyethylacrylamide, N-hydroxyethylmethacrylamide, N-hydroxypropylacrylamide and N-hydroxypropylmethacrylamide.

Other compounds suitable as monomers (c) are:

$C_1$–$C_{30}$ vinyl esters, such as vinyl acetate, vinyl propionate, vinyl butyrate, vinyl valerate, vinyl 2-ethylhexanoate, vinyl decanoate, vinyl palmitate, vinyl stearate and vinyl laurate;

$C_1$–$C_{30}$ vinyl ethers, such as methyl vinyl ether, ethyl vinyl ether, N-propyl vinyl ether, isopropyl vinyl ether, n-butyl vinyl ether, isobutyl vinyl ether, 2-ethylhexyl vinyl ether, decyl vinyl ether, dodecyl vinyl ether, stearyl vinyl ether, 2-(diethylaminc)ethyl vinyl ether, 2-(di-n-butylemiino) ethyl vinryl ether and methyldiglycol vinyl ether;

vinyl aromatic compounds, for example styrene and substituted styrenes, such as p-methylstyrene and α-methylstyrene, and Si-containing monomers, especially unsaturated polysiloxanes.

Preferred monomers (c) are styrene and acrylamides.

The monomers (c) are employed in the copolymers in an amount of 0–50% by weight, preferably 0–40% by weight, based on the overall weight of all monomers.

Both individual compounds and mixtures of individual compounds can be employed as monomers (c).

The novel copolymers can be prepared by the known techniques of emulsion, solution, suspension or precipitation polymerization, using auxiliaries familiar to the skilled worker.

The solution polymers or emulsion polymers can either be converted, in an additional step, to a solid or employed directly in the cosmetic formulations.

The K value (determined in 1% strength ethanolic solution at 25° C. in accordance with H. Fikentscher, Cellulose-Chemie 13 (1932), pp. 58–64 and 71, 74) can be controlled by means of known variations in technique. The copolymers employed in accordance with the invention have a K value of 20–150, preferably 30–120.

The carboxyl groups of the copolymer can be neutralized using all common neutralizing agents. Particularly suitable are alkali metal hydroxides, ammonia, alkali metal carbonate or ammonium carbonate, $C_1$–$C_6$ mono-, di- or trialkylamines, alkanolamines, tetrahydroxypropylethylenediamine, basic heterocycles or mixtures of these substances. The neutralizing agents can be added in pure or dissolved form. It is preferred to add them in the form of aqueous solutions. Particular preference is given to alkali metal hydroxides and 2-amino-2-methylpropan-1-ol.

The copolymers can be neutralized directly after polymerization or not until the hair cosmetic is being formulated. It is generally undertaken by adding the neutralizing agent until the desired pH is reached. The target pH in the finished formulation is generally 5.5–8.0.

The hair-cosmetic formulations include solvents comprising water or mixtures of water and alcohol, the proportion of water in the mixture usually being 20% by weight or more.

To modify the cosmetic properties it is possible to add other film-forming hairsetting or conditioning polymers to the hair cosmetic.

The hair-cosmetic formulations also usually include one or more of the following ingredients familiar to the skilled worker:

organic solvents, propellant gases, gel formers, thickeners, preservatives, colorants, perfume oils, opacifiers, active substances, UV filters and surface-active compounds, ie. foam formers, emulsifiers, surfactants, solubilizers and the like. The surface-active compounds employed can be anionic, cationic, amphoteric or neutral.

EXAMPLES 1–6

Preparation of Copolymers 6 different copolymers were prepared. Details of the preparation technique, monomer ratio and K values are given in Table 1.

TABLE 1

| Example | Monomer | Ratio (% by wt.) | Technique | K value |
|---------|---------|------------------|-----------|---------|
| 1 | EA/MAA | 50/50 | EP | 60 |
| 2 | EA/MAA | 50/50 | EP | 90 |

TABLE 1-continued

| Example | Monomer | Ratio (% by wt.) | Technique | K value |
|---------|---------|------------------|-----------|---------|
| 3 | tBA/MAA | 60/40 | EP | 40 |
| 4 | N-tBAM/EA/MAA | 10/30/60 | SoP | 35 |
| 5 | tBMA/MAA | 35/65 | PrP | 105 |
| 6 | S/AA/MAA/BA | 40/20/25/15 | SP | 66 |

Key to monomers:
AA: acrylic acid; MAA methacrylic acid; EA: ethyl acrylate; tBA tert-butyl acrylate; NtBAM: N-tert-butylacrylamide; tBMA: tert-butyl methacrylate; S: styrene; BA: butyl acrylate
Key to techniques:
EP: emulsion polymerization; SoP: solution polymerization; PrP: precipitation polymerization; SP: suspension polymerization Formulation of Various Hairsetting Compositions The copolymers of Table 1 were employed in the following formulations and tested on model heads, ie. natural human hair.

The percentages are by weight.

(Ex. 7.1–7.6) Formulation as Hairsetting Lotion

35% ethanol

3% polymer (from Examples 1–6)

x aminomethylpropanol (AMP) pH about 7.0

0.3% PEG40-hydrogenated castor oil (Cremophor RH 40, BASF AG)

q.s. perfume oil ad 100% water (EX. 8.1–8.6) Formulation as Styling Lotion

4% polymer (from Examples 1–6)

x aminomethylpropanol (AMP) pH about 6.5

0.3% PEG40-hydrogenated castor oil (Cremophor RH 40, BASF AG)

q.s. perfume oil ad 100% water (Ex. 9.1–9.6) Formulation as Styling Mousse

5% ethanol

3% polymer (from Examples 1–6)

x aminomethylpropanol (AMP) pH about 6.3

0.3% Ceteareth 25 (Cremophor A25, BASF AG)

10% propane/butane (25/75)

ad 100% water

A degree of neutralization of 60% (AMP) leads, in the case of the particularly preferred polymer from Example 1 in a 3% strength aqeuous solution, to a pH of 6.3.

In the performance test, about 3 g of each formulation were applied to one side of the model head.

The formulations were assessed for hairsetting, conditioning, dry combability, tack and wash out.

The formulations show excellent hairsetting. The dry combability is assessed as being excellent and after combing the hair does not feel tacky but instead feels very sleek.

Moreover, the products can be washed out from the hair, without residue, using conventional shampoos.

We claim:

1. An aqueous or aqueous-alcoholic hair-cosmetic formulation comprising as film former copolymers based on (meth)acrylate which have a K value of 20–150 and are obtained by free-radical polymerization of monomers consisting essentially of (a) 40–65% by weight of acrylic acid and/or methacrylic acid;

(b) 14–60% by weight of one or more alkyl (meth) acrylates; and (c) 0–50% by weight of one or more free-radically polymerizable monomers;

20–100% of the carboxyl groups of the copolymer being neutralized.

2. The hair-cosmetic formulation of claim 1, wherein the copolymer comprises (a) 45–60% by weight of acrylic acid and/or methacrylic acid;

(b) 20–55% by weight of one or more alkyl (meth) acrylates; and (c) 0–40% by weight of one or more free-radically polymerizable monomers;

and wherein 20–60% of the carboxyl groups of the copolymer are neutralized.

3. The hair-cosmetic formulation of claim 1, where neutralizing agents employed are alkali metal hydroxides, ammonia, alkali metal carbonate or ammonium carbonate, C1–C6 mono-, di- or tri-alkylamines, alkanolamines, tetrahydroxy-propylethylenediamine, basic heterocycles or mixtures thereof.

4. The hair-cosmetic formulation of claim 1, where the copolymer has been prepared by emulsion, solution, precipitation or suspension polymerization.

5. The hair-cosmetic formulation of claim 1, which additionally comprises other film-forming hairsetting and/or conditioning polymers.

6. The hair-cosmetic formulation of claim 1, which is a styling lotion, a hairsetting lotion or a styling mousse.

* * * * *